(12) United States Patent
Stone

(10) Patent No.: US 6,929,623 B2
(45) Date of Patent: Aug. 16, 2005

(54) ELONGATED SYRINGE

(75) Inventor: Corbett Stone, San Diego, CA (US)

(73) Assignee: Artes Medical, Inc., San Diego, CA (US)

( * ) Notice: Subject to any disclaimer, the term of this patent is extended or adjusted under 35 U.S.C. 154(b) by 0 days.

(21) Appl. No.: 10/992,915

(22) Filed: Nov. 18, 2004

(65) Prior Publication Data

US 2005/0090780 A1 Apr. 28, 2005

Related U.S. Application Data

(63) Continuation of application No. 10/205,597, filed on Jul. 24, 2002.
(60) Provisional application No. 60/377,016, filed on Apr. 29, 2002, and provisional application No. 60/307,225, filed on Jul. 24, 2001.

(51) Int. Cl.$^7$ .............................................. A61M 51/78
(52) U.S. Cl. ................. 604/164.01; 604/239; 604/272; 604/135
(58) Field of Search ................................ 604/218, 235, 604/239, 191, 272, 164.01, 135

(56) References Cited

U.S. PATENT DOCUMENTS

| | | | | |
|---|---|---|---|---|
| 2,603,782 A | * | 7/1952 | Spencer | 227/132 |
| 3,625,208 A | * | 12/1971 | Frost et al. | 604/68 |
| 3,782,380 A | * | 1/1974 | Van Der Gaast | 604/68 |
| 4,560,378 A | * | 12/1985 | Weiland | 604/83 |
| 4,767,407 A | * | 8/1988 | Foran | 604/164.06 |
| 4,769,011 A | * | 9/1988 | Swaniger | 604/218 |
| 4,801,263 A | * | 1/1989 | Clark | 433/90 |
| 5,286,257 A | * | 2/1994 | Fischer | 604/82 |
| 5,312,345 A | * | 5/1994 | Cole | 604/110 |
| 5,389,076 A | * | 2/1995 | Shaw | 604/110 |
| 5,447,496 A | * | 9/1995 | Bove et al. | 604/514 |
| 5,697,965 A | * | 12/1997 | Griffin, III | 607/123 |
| 5,720,731 A | * | 2/1998 | Aramata et al. | 604/191 |
| 5,830,193 A | * | 11/1998 | Higashikawa | 604/191 |
| 5,916,208 A | * | 6/1999 | Luther et al. | 604/508 |
| 5,951,528 A | * | 9/1999 | Parkin | 604/239 |
| 6,168,432 B1 | * | 1/2001 | Marlin | 433/81 |
| 6,203,533 B1 | * | 3/2001 | Ouchi | 604/264 |
| 6,500,157 B2 | * | 12/2002 | Luther | 604/264 |
| 6,508,802 B1 | * | 1/2003 | Rosengart et al. | 604/523 |
| 6,524,284 B1 | * | 2/2003 | Marshall | 604/272 |
| 6,666,848 B2 | * | 12/2003 | Stone | 604/164.01 |

* cited by examiner

Primary Examiner—Sharon Kennedy
(74) Attorney, Agent, or Firm—Stout, Uxa, Buyan & Mullins, LLP

(57) ABSTRACT

An elongated syringe for administering a substance to a patient includes an elongated syringe chamber that may be inserted into a duct of a patient without unwantingly injuring the patient, a needle extending from the distal end of the syringe chamber, and a plunger rod extending from the proximal end of the syringe chamber. The syringe chamber may be flexible to accommodate curvatures of the duct of the patient. The syringe chamber includes a plurality of chamber compartments that will contain a fluid. At least one of the chamber compartments contains a fluid that is administered to a patient. The syringe chamber may include a driving piston located between two or more chamber compartments. The needle of the syringe may be a component of a transition-bore needle apparatus to facilitate delivery of a relatively viscous fluid from the syringe. The needle may also be flared at its proximal end so that the diameter of the proximal end of the needle is greater than the diameter of the distal end of the needle. Methods of using an elongated syringe are disclosed.

8 Claims, 6 Drawing Sheets

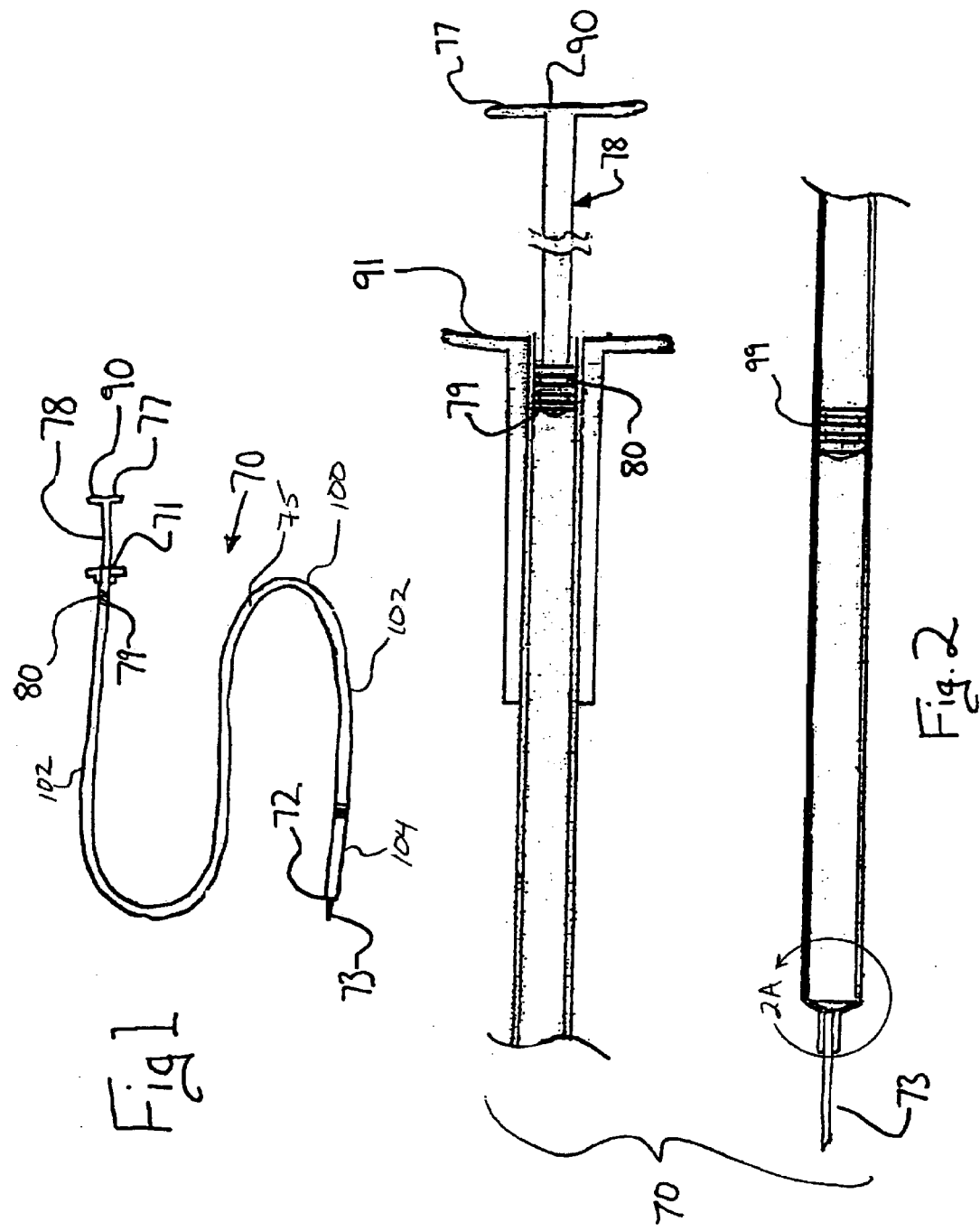

ELONGATED SYRINGE

CROSS-REFERENCE TO RELATED APPLICATIONS

This application is a continuation of U.S. patent application No. 10/205,597, entitled ELONGATED FLEXIBLE SYRINGE, and filed Jul. 24, 2002: which claims the benefit of U.S. Provisional Application No. 60/307,225, entitled ELONGATED FLEXIBLE SYRINGE, and filed Jul. 24, 2001; and U.S. Provisional Application No. 60/377,016, entitled ELONGATED FLEXIBLE SYRINGE WITH BEVEL-CUT NEEDLE TRANSITION, and filed Apr. 29, 2002, the entire contents of which are hereby incorporated by reference.

BACKGROUND OF THE INVENTION

1. Field of the Invention

The present invention relates generally to medical devices and, more particularly, to syringes and needles.

2. Description of Related Art

The term "stress urinary incontinence" refers to a functionally insufficient urinary tract of a patient. In a patient having this condition, the tissue relaxation of the sphincter mechanism, located at the urinary outflow of the bladder into the urethra, can cause a loss of bladder control. Cystoscopes are typically used to study the urethra and bladder and to evaluate a patient's urinary incontinence condition. A typical cystoscope may comprise a tubular instrument equipped with, for example, a visual channel and a working channel, and constructed to be inserted through the urethra for viewing of the urethra and bladder. Treatment of a urinary incontinence condition may comprise the injection of a filler material, such as collagen, into and adjacent to the urinary sphincter muscle at the bladder neck, to thereby bulk up the tissue and assist in the adequate closure of the urinary sphincter.

Acid reflux is a digestive disorder which similarly involves the tissue relaxation of a sphincter mechanism. In the case of acid reflux, which is commonly known as gastroesophageal reflux disease (GERD) or heartburn, the lower esophageal sphincter connecting the esophagus to the stomach begins to malfunction. During proper operation of the lower esophageal sphincter, the lower esophageal sphincter opens to allow food to pass into the stomach and closes to prevent food and acidic stomach fluids from flowing back up into the esophagus. Gastroesophageal reflux occurs when the lower esophageal sphincter is weak or relaxes inappropriately, allowing the stomach's contents to retrograde or flow up into the esophagus. This retrograde flow of gastric contents back into the esophagus, through what should be a one-way valve into the stomach, can damage the esophagus. More particularly, the contents of the stomach are very acidic; and the lining of the stomach is specially designed to cope with the lower pH contents. The esophagus, on the other hand, is not suited for such exposure to highly acidic materials. Thus, when acid retrogrades from the stomach into the esophageal tissues, irritation and inflammation will often result to these tissues.

The severity of tissue damage which can result from gastroesophageal reflux disease can depend on factors such as the dysfunctional level of the lower esophageal sphincter, the type and amount of fluid brought up from the stomach, and the neutralizing effect of the patient's saliva. Another factor, which may affect the severity of a particular gastroesophageal reflux disorder, is the patient's esophageal motility. Lack of esophageal motility can occur through either of two mechanisms. When incomplete emptying of the esophagus into the stomach after ingestion of liquids or solids occurs, the motility of the esophagus can be said to be effected, resulting in esophageal reflux. Also, esophageal reflux can occur when small amounts of gastric contents, which may be refluxed into the lower esophagus, are not rapidly emptied back into the stomach. Delays in the emptying of this material, caused by an esophageal motility disorder, for example, can lead to irritation of the esophageal mucosa and possibly to the sensation of heartburn or the development of esophagitis.

Various tools and instruments have been used in the prior art for the treatment of urinary incontinence and acid reflux disease. Gastroscopes are typically used to study the esophagus and to evaluate, for example, a patient's acid reflux condition. A gastroscope typically comprises a flexible, lighted instrument that is inserted through the mouth and esophagus to view the stomach. Similarly, a cystoscope is typically inserted through a patient's urethra to facilitate evaluation of, for example, a urinary incontinence condition.

A viscous material, such as collagen, may be injected into the vicinity of either the lower esophageal sphincter (for acid reflux) or the sphincter of the urethra (for urinary incontinence) to treat either of the above-mentioned disorders. These injection procedures typically involve elongated catheters for the delivery of viscous materials through the body passages and to the target sites of injection. The force required to deliver a viscous material through the delivery lumen of an elongated catheter will increase as the average viscosity of the material being delivered is increased and will also increase as the length of the elongated catheter increases.

To compensate for the greater required force, it would be desirable to form the elongated catheter to have a lumen with a relatively large cross-sectional area to facilitate flow of the viscous material therethrough. Another design criterion is that the diameter of the needle tip should be relatively small to reduce tissue trauma at the injection site, to increase precision in some instances, and to reduce patient discomfort.

In order to meet the objectives of both a relatively large delivery lumen and a relatively small needle tip, a juncture must be formed at some point along the length of the needle to transition the needle diameter from a relatively large size to a relatively small size. If the transition point is abrupt or too great in magnitude, optimal flow of the viscous material through the needle may be inhibited.

SUMMARY OF THE INVENTION

An elongated syringe, as disclosed herein, is dimensioned to be inserted into a duct of a patient, including, but not limited to, a patient's urethra, esophagus, and blood vessels. The syringe includes a syringe chamber having two or more chamber compartments for containing a fluid, a needle extending from the distal end of the syringe chamber, and a plunger rod extending from the proximal end of the syringe chamber. The syringe chamber may also include a driven piston positioned between two chamber compartments that is driven by displacement of the plunger rod. The syringe may be flexible to accommodate curvatures of the patient's ducts. The needle of the syringe is structured to facilitate delivery of relatively viscous substances to a patient. The needle may be flared at its proximal end so that the proximal end has a greater diameter than the distal end. The needle may be a component of a transition-bore needle apparatus, as disclosed herein. Such a needle may have a proximal end that is beveled, chamfered, or beveled and chamfered.

In order to reduce the force required to eject a viscous material through the delivery lumen of an elongated syringe chamber, a transition-bore needle apparatus may be provided. The transition-bore needle apparatus can be attached to an elongated flexible syringe, to thereby optimize the flow of a viscous material through a decreasing-diameter lumen of a needle that is attached to a distal end of the elongated flexible syringe. The transition-bore needle apparatus comprises a proximal end and a distal end, and the lumen extends from the proximal end of the transition-bore needle apparatus to the distal end of the transition-bore needle apparatus. A diameter at a proximal portion of the transition-bore needle apparatus is greater than a diameter at a distal portion of the transition-bore needle apparatus.

In accordance with one aspect of the present invention, the proximal portion of the transition-bore needle apparatus comprises a first needle having a first diameter, and the distal portion of the transition-bore needle apparatus comprises a second needle having a second diameter. The first diameter is greater than the second diameter. The first needle comprises a proximal end, a distal end, and a first lumen extending through the first needle from the proximal end to the distal end, and the second needle similarly comprises a proximal end, a distal end, and a second lumen extending through the second needle from the proximal end of the second needle to the distal end of the second needle.

The lumen of the transition-bore needle apparatus comprises both a portion of the first lumen of the first needle and a portion of the second lumen of the second needle. A juncture thus exists within the lumen of the transition-bore needle apparatus, where the diameter thereof transitions from the first diameter to the second diameter. At this juncture, the proximal end of the second needle terminates within the first lumen. In accordance with an aspect of the present invention, the proximal end of the second needle is bevel-cut at an acute angle relative to the longitudinal axis of the second needle, forming a bevel-cut needle transition. The bevel-cut needle transition may improve a flow of viscous material through the lumen of the transition-bore needle apparatus by providing a gradual transition from the larger first diameter to the smaller second diameter. In accordance with another aspect of the present invention, the proximal end of the first needle is chamfered to improve a flow of viscous material through the lumen of the transition-bore needle apparatus. According to yet another aspect of the present invention, the proximal end of the first needle is both chamfered and beveled to improve a flow of viscous material through the lumen of the transition-bore needle apparatus.

The second needle may comprise a beveled edge at the bevel-cut needle transition to improve a flow of viscous material through the lumen of the transition-bore needle apparatus. In accordance with another aspect of the present invention, the bevel-cut needle transition is chamfered to improve a flow of viscous material through the lumen of the transition-bore needle apparatus. According to yet another aspect of the present invention, the bevel-cut needle transition is both chamfered and beveled to improve a flow of viscous material through the lumen of the transition-bore needle apparatus.

The elongated syringe, which attaches to the transition-bore needle apparatus, operates by using a compressing structure (in combination with a compartment of the delivery lumen comprising the lower-viscosity material) to drive a viscous material through the distal end of the lumen of the elongated flexible syringe and into the transition-bore needle apparatus. Both the elongated flexible syringe and the transition-bore needle apparatus of the present invention facilitate the injection of viscous filler material by optimizing a flow of the viscous material therethrough. The elongated flexible syringe and transition-bore needle apparatus may be used in conjunction with surgical instruments, such as endoscopes, cystoscopes, and gastroscopes, to aid in intraluminal injections of materials into body tissues within body lumens.

The present invention thus facilitates the injection of viscous filler materials, and may provide for increased speed, accuracy and efficiency in dispensing such materials. The injection of bulking agents into the respective tissues of body sphincters helps to fortify the respective tissue structures and re-establish normal sphincter control. The subjects and objects of this disclosure therefore relate to novel methods and instruments for facilitating the controlled dispensing of viscous material in the interior of the body, including but not limited to soft tissues, and ducts or lumen structures (e.g., esophagus, urethra).

The present invention, together with additional features and advantages thereof, may best be understood by reference to the following description taken in connection with the accompanying illustrative drawings.

BRIEF DESCRIPTION OF THE DRAWINGS

FIG. 1 illustrates an elongated flexible syringe in accordance with the present invention;

FIG. 2 illustrates a cross-sectional view of the elongated flexible syringe of FIG. 1;

DETAILED DESCRIPTION OF THE PRESENTLY PREFERRED EMBODIMENTS

Figure 3B:
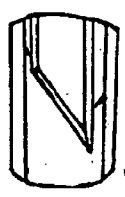
FIG. 3B is a cross-sectional view of a proximal end of a distal needle having an edge that is chamfered at about a 30 degree angle from the longitudinal axis of the distal needle.

Referring more particularly to the drawings, FIG. 1 illustrates an elongated flexible syringe 70 comprising a syringe chamber 100 having a proximal end 71, a distal end 72, and a lumen 75 extending between the proximal end 71 and the distal end 72. It is to be understood that, as used herein, the term "proximal" means the end or part nearest to the operator of the instrument and the term "distal" means the end or part furthest from the operator. Thus, the front end of the instrument that enters the body canal is the distal end.

The elongated flexible syringe 70 serves to facilitate injections of viscous materials, such as viscous fluids, through body passages. As used herein, the term "fluid" refers to liquids and gasses. Examples of fluids include water, saline, buffers, such as sodium or phosphate buffers, other water based compositions, and viscous materials, such as collagen compositions. In the illustrated embodiment, the elongated flexible syringe 70 is about one meter long with a movable rod 78 fitted within the proximal end 71 of the elongated flexible syringe 70 and a needle 73, such as, for example, the transition-bore needle apparatuses of FIGS. 3 and 4, disposed at the distal end 72 of the elongated flexible syringe 70. The movable rod 78 comprises a proximal rod end 77 and a distal rod end 79. A hand-held compressing structure 90 is disposed at the proximal rod end 77 of the movable rod 78.

At the distal rod end 79 of the movable rod 78, fitted within the elongated flexible syringe 70, is a driving piston 80 comprising rings, which in the illustrated embodiment are constructed similarly to the rings of the movable rod of a conventional syringe. The rings are structured and dimensioned to create a fluid-tight seal within the syringe chamber 100 so that displacement of the plunger rod 78 and driving piston 80 will cause a corresponding displacement of fluid contained within the syringe chamber. In accordance with one exemplary embodiment, the driving piston 80 comprises Nitrile synthetic rubber. A finger-rest 91 is disposed on the outside of the distal end 79 of the elongated flexible syringe 70. Although the elongated syringe chamber 100 preferably comprises a flexible material, such as polypropylene and/or a multi-layer extrusion with an anti-friction inner surface (e.g., a Teflon inner layer), the finger rest 91 and movable rod 78 preferably comprise a relatively rigid material such as a relatively rigid plastic. The construction of the finger rest 91 may be changed so that the finger rest 91 extends proximally a greater length in modified embodiments.

The lumen 75 of the elongated flexible syringe chamber 100 is filled with a displaceable fluid, such as saline, from the proximal end 71 to near the distal end 72. In the illustrated embodiment, a few inches, such as between 1 and 5 inches, and preferably between 1 and 3 inches, proximally of the distal end 72 of the elongated flexible syringe 70 is a driven piston 99, which preferably is constructed similarly to the driving piston 80 and which separates the saline from a viscous material that is disposed distally of the driven piston 99.

Driven piston 99 is driven by the movement of driving piston 80. Accordingly, driven piston 99 creates a plurality of chamber compartments within syringe chamber 100. In the illustrated embodiment, driven piston 99 creates a first chamber compartment 102 that contains the displaceable fluid, and a second chamber compartment 104 that contains a substance that is administered to a patient. Although the illustrated embodiment of the syringe has two chamber compartments, other embodiments may include three or more chamber compartments depending on the particular characteristics of the substance(s) being administered. In addition, although a fluid, such as saline, is disclosed as being a displaceable fluid (e.g., to displace the driven piston 99), other suitable fluid may be used. It may be desirable that the fluid is relatively incompressible to cause a one-to-one displacement of the driven piston compared to the driving piston; however, fluids, such as gases, may be utilized that provide progressive displacement ratios (e.g., where a two centimeter displacement of the driving piston causes a one centimeter displacement of the driven piston). Additionally, other materials may be utilized that are not fluids, so long as the material does not prevent the syringe chamber from flexing. For example, a solid rubber insert may be slidably inserted into first chamber compartment 102. Other similar materials may also be used.

Although the elongated flexible syringe 70 is designed to facilitate accurate dispensing of viscous materials, such as filler materials, the elongated flexible syringe 70 further may be used to accurately dispense other materials and fluids as well. In the illustrated embodiment, the viscous material comprises collagen and/or micro-spheres, such as disclosed in U.S. Pat. No. 5,344,452, the contents of which are expressly incorporated herein by reference, or, for example, any other type of injectable bulking agent. The elongated flexible syringe can be supplied pre-loaded with the viscous material (disposed distally of the driven piston 99), or the viscous material may be drawn proximally into the portion of the lumen that is distal of the driven piston 99. In another embodiment, the viscous material may be inserted into the proximal end of the lumen (with the driven piston 99 and the movable rod 78 removed) and forced distally through the lumen with a long piston (e.g., similar in construction to the movable rod 78 but longer). Subsequently, the driven piston 99 and the movable rod 78 are positioned within the lumen to hold the viscous material at the distal end of the elongated flexible syringe.

Figure 2A:
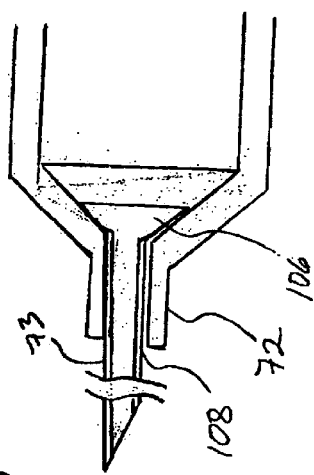
FIG. 2A is a magnified view along line 2A of FIG. 2.

The distal end 72 of the elongated flexible syringe 70 in the illustrated embodiment is shaped to snugly accommodate the needle 73 therein (e.g., see FIG. 2A). The needle 73 fits at the distal end 72 of the elongated flexible syringe 70 to form a transitional cone for facilitating distal movement and ejection of the viscous material out of a relatively small diameter distal output end of the transition-bore needle apparatus. In the illustrated embodiment, the needle 73 comprises a conical or flared proximal end 106. For example, the proximal end of the needle may be flared like a trumpet. Or, in other words, the proximal end of the needle can be flared so that the diameter of the proximal end is greater than the diameter of the distal end of the needle. Although the illustrated needle is shown as having a flared proximal end 106, and a portion 108 between the proximal end and the distal end that has a constant diameter, other needles may be structured to have a continuous taper along any length of the needle from the proximal end towards the distal end of the needle. The needle 73 can be secured to the distal end 72 of the elongated flexible syringe chamber using a number or procedures. For example, the needle can be inserted into the proximal end of the lumen 75 (with the movable rod 78 and the driven piston 99 removed) and then pulled distally through the lumen 75 with a wire, until it is secured at the distal end by any conventional mechanical means such as a press fit (e.g., swaging procedure) and/or an adhesive. As another example, the needle can be held in place while the distal end of the elongated flexible syringe is press fitted/clamped around the needle. In another preferred embodiment, the needle 73 comprises a transition-bore needle apparatus.

Upon application of both a distal pressure against the hand-held compressing structure 90 and a proximal pressure against the finger-rest 91, the movable rod 78 and the driving piston 80 move the saline within the lumen 75 against the driven piston 99. The saline in turn pushes the driven piston 99 in the distal direction. As mentioned, other fluids or materials may be used within the lumen 75 as an alternative to, or in addition to, the saline so long as the driven piston 99 can be moved in response to distal movement of the hand-held compressing structure 90. Thus, in the illustrated embodiment, movement of the hand-held compressing structure 90 five millimeters in the distal direction will push the saline approximately five millimeters in the same direction, which in turn will push the driven piston 99 about five millimeters in the distal direction, to thereby eject a corresponding portion of the viscous material from the needle 73.

Use of the elongated flexible syringe 70 can result in less pressure being applied throughout the apparatus. Filling the entire syringe with the viscous material may be time intensive and costly and further may result in difficulty of operation because of the viscous material's resistance to flow. The saline within the lumen 75 facilitates easier loading and injection procedures, since the saline fills most of the lumen 75 and has a smaller resistance to flow. The elongate flexible syringe 70 may comprise or be connected to, for example, the flexible tube 40 of FIG. 3 or the proximal tube 13 of FIG. 4.

The elongated syringe 70 of the present invention thus facilitates the injection of viscous filler materials, and provides for increased accuracy in the amounts of such dispensed materials. An exemplary embodiment of the invention comprises an elongated syringe that can be introduced through a patient's urethra in the treatment of urinary incontinence. As another example, a treatment for gastro-esophageal reflux disease may be fashioned to increase the strength or length of the lower esophageal sphincter (LES) via the deposition of a viscous bulking material into surrounding tissues of the lower esophageal sphincter. An elongated syringe of the present invention is suitable for such use in conjunction with a needle tip. The viscous suspension can be injected directly into the specific areas where the viscous agent is desired. Principal uses of the present invention are to accurately and conveniently dispense the viscous material to thereby alter the operational architecture of the patient's sphincter. Thus, the biomechanical characteristics of the sphincter are altered to alleviate the disorder.

The elongated syringe 70 can increase the precision of dispensing fluids from, for example, the transition-bore needle apparatus, as it can be calibrated to permit a specific concentration of material to be dispensed from the needle. This is especially important due to the high level of viscosity of the material being passed through the elongated syringe, the distance of the elongated syringe, and the general need for surgical precision when injecting bulking agents. Further, the elongated syringe can facilitate effective dispensation by reducing the amount of strength or effort required to secrete the viscous material out the syringe.

Figure 3A:
FIG. 3A is a cross-sectional view of a proximal end of a distal needle having an edge that is beveled at about a 30 degree angle from a longitudinal axis of the distal needle.
Figure 3:
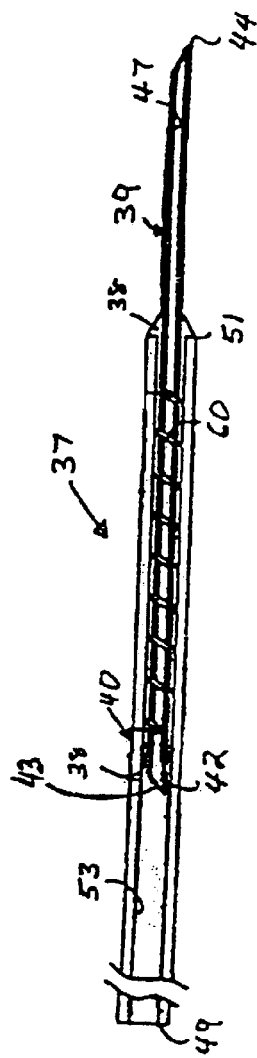
FIG. 3 illustrates a transition-bore needle apparatus for use in the treatment of urinary incontinence in accordance with the present invention.
Figure 7A:
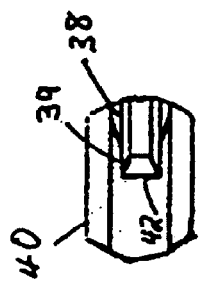
FIG. 7A is a cross-sectional view of a proximal end of a needle with edges chamfered at about a 30 degree angle from the longitudinal axis of the needle.
Figure 7B:
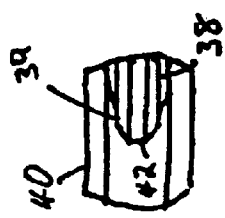
FIG. 7B is a cross-sectional view of a proximal end of a needle with edges beveled at about a 30 degree angle from the longitudinal axis of the needle.
Figure 7:
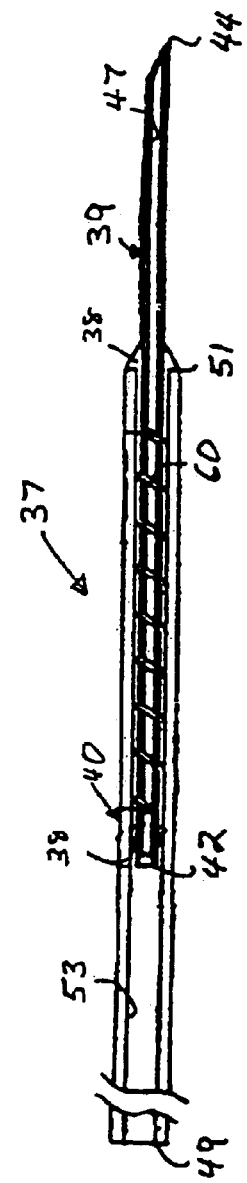
FIG. 7 illustrates a transition-bore needle apparatus for use in combination with an elongated flexible syringe for the treatment of gastro-esophageal reflux disease in accordance with the present invention.

FIG. 3 and FIG. 7 illustrate a transition-bore needle assembly 37 for use in applications such as lower esophageal injections of bulking material. The transition-bore needle assembly 37 comprises a needle 39 connected to a flexible tube 40. The flexible tube 40 may comprise a polymeric material, such as polyethylene terephthalate (PET). The needle 39 comprises a proximal end 42, a distal end 44, and a lumen 47 extending between the proximal end 42 and the distal end 44. The distal end 44 of the needle 39 may comprise a cutting edge needle tip, which is suitable for puncturing skin and other soft tissues such as muscle tissue. As presently embodied, the cutting edge needle tip is formed at a 20 degree angle from a longitudinal axis of the needle 39. In an alternative embodiment, the distal end 44 of the needle 39 may comprise a round point needle tip. The flexible tube 40 similarly has a proximal end 49, a distal end 51, and a lumen 53 extending from the proximal end 49 to the distal end 51.

As presently embodied, the needle 39 comprises surgical stainless steel, such as 304 grade surgical stainless steel or 316 grade surgical stainless steel. The proximal end 42 of the needle 39 is inserted into and attached to the distal end 51 of the flexible tube 40, so as to create a transitional cone to facilitate the movement of viscous bulking material, such as material containing suspended beads or micro-spheres, through the transition-bore needle apparatus 37 in a direction from the flexible tube 40 to the needle 39. The lumen of the transition-bore needle apparatus 37 comprises both a portion of the lumen 47 of the needle 39 and a portion of the lumen 53 of the flexible tube 40, as can be seen from FIG. 3. A juncture thus exists within the lumen of the transition-bore needle apparatus 37, where the diameter thereof transitions from a diameter of the flexible tube 40 to a diameter of the needle 39. At this juncture, the proximal end 42 of the needle 39 terminates within the lumen 53 of the flexible tube 40.

In the illustrated embodiment, the needle 39 has an inner diameter of about 0.012 inches and an outer diameter of about 0.020 inches, and the flexible tube 40 has an inner diameter of 0.032 inches and an outer diameter of 0.056 inches. A wire 60 is wrapped around the needle 39 and glued into place. In the gluing process, the glue 38 is preferably allowed to dry and then heat cured. Another glue is then applied to the surfaces of the resulting wire 60 and needle 39. The glue may comprise, for example, a lock-tight glue or a superglue. The needle 39 is then gripped and held with, for example, a chuck, and screwed into the flexible tube 40, which may comprise a polymeric tube having, for example, a smooth inner surface. Some glue will remain on the distal end 51 of the flexible tube 40 to form a seal, after the needle 39 and wire 60 are screwed in. The wire 60 around the needle 39 preferably deforms the smooth inner surface of the flexible tube 40 for a frictional fit.

As illustrated in FIG. 3, the proximal end 42 of the needle 39 comprises a bevel-cut needle transition 43 to improve a flow of viscous material through the lumen of the transition-bore needle apparatus 37. Cutting the proximal end 42 of an initially cylindrical needle 39 at an angle to the longitudinal axis of the needle 39, for instance, may form the bevel-cut needle transition 43. The bevel-cut needle transition 43 may be at an angle less than ninety degrees and, preferably, less than sixty degrees, and more preferably, about 45 degrees. The needle 39 with bevel-cut needle transition 43, may then be secured within the lumen 53 of the flexible tube 40. In modified embodiments, the angle may be reduced to, for example, 30 degrees or 15 degrees from the longitudinal axis of the needle 39. However, as illustrated in FIGS. 7, 7A, and 7B, needles having proximal ends disposed at ninety degrees from the longitudinal axis of the needle are possible in modified embodiments of the invention.

According to another aspect of the present invention, the needle 39 with bevel-cut needle transition 43 is beveled to improve a flow of viscous material through the lumen of the transition-bore needle apparatus 37. FIG. 3A is a cross-sectional view of a bevel-cut needle transition 43 with edge beveled at about a 30 degree angle from the longitudinal axis of the needle 39. FIG. 7A is a cross-sectional view of a proximal end of a needle oriented at about a ninety degree angle from the needle's longitudinal axis. After the needle is bevel cut (with respect to the needle of FIG. 3A), the exposed edges are beveled. This beveling may be performed by filing the edge of the bevel-cut needle transition 43 to an angle less than ninety degrees and, preferably, less than sixty degrees, and more preferably, about 45 degrees. In modified embodiments, the angle may be reduced to, for example, 30 degrees or about 15 degrees.

In accordance with another aspect of the present invention, the needle 39 with bevel-cut needle transition 43 is chamfered to improve a flow of viscous material through the lumen of the transition-bore needle apparatus 37. FIG. 3B is a cross-sectional view of a bevel-cut needle transition 43 with edge beveled at about a 30 degree angle from the longitudinal axis of the needle 39. FIG. 7B is a cross-sectional view of a proximal end of a needle oriented at about a ninety degree angle from the needle's longitudinal axis. After the needle is bevel cut (with respect to FIG. 3B), the exposed edges are chamfered. The chamfering may be performed by filing the edge of the bevel-cut needle transition 43 to an angle less than ninety degrees and, preferably, less than sixty degrees, and more preferably, about 45 degrees. In modified embodiments, the angle may be reduced to, for example, 30 degrees, or even about 15 degrees from the longitudinal axis of the distal needle 39. According to yet another aspect of the present invention, the proximal end 42 of the bevel-cut needle 39 is both chamfered and beveled, in accordance with the structures discussed in the preceding paragraph, to thereby improve a flow of viscous material through the lumen of the transition-bore needle apparatus 37.

Figure 4B:
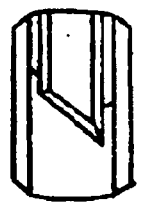
FIG. 4B is a cross-sectional view of a proximal end of a distal needle having a bevel-cut transition, which comprises an edge that is chamfered at about a 45 degree angle from a longitudinal axis of the needle.
Figure 4:
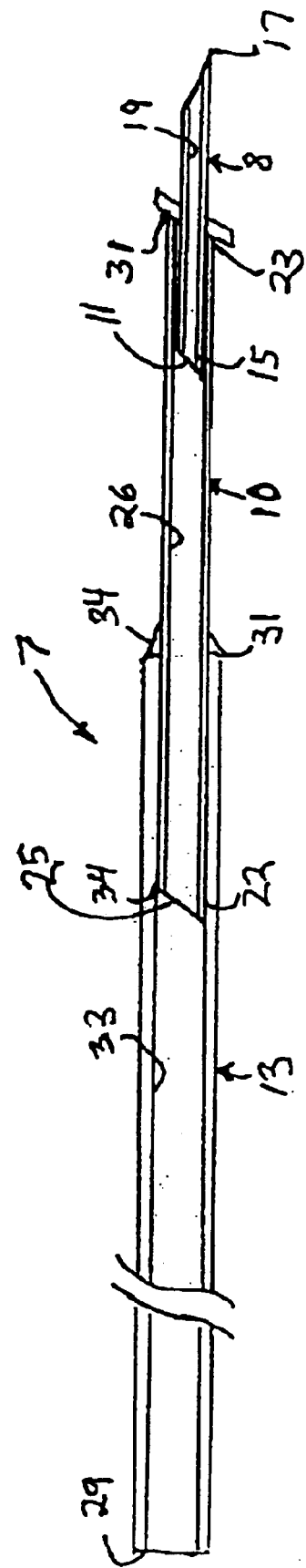
FIG. 4 illustrates a transition-bore needle apparatus for use in the treatment of urinary incontinence in accordance with the present invention.

Turning now to FIG. 4, a transition-bore needle apparatus 7 is illustrated, adapted for use in applications such as urethral injections, and having a distal needle 8, an intermediate tube 10, and a proximal tube 13. The distal needle 8 comprises a proximal end 15, a distal end 17, and a lumen 19 extending from the proximal end 15 to the distal end 17. The distal end 17 of the distal needle 8 comprises a cutting edge needle tip, which is suitable for puncturing skin and other soft tissues such as muscle tissue. In an alternative embodiment, the distal end 17 of the distal needle 8 may comprise a round point needle tip for use in connection with more delicate surgical operations. The intermediate tube 10 comprises a proximal end 22, a distal end 23, and a lumen 26 extending from the proximal end 22 to the distal end 23. The proximal tube 13, which may correspond for example to the needle 73 of FIG. 2, comprises a proximal end 29, a distal end 31, and a lumen 33 extending from the proximal end 29 to the distal end 31.

As presently embodied, the distal needle 8, the intermediate tube 10, and the proximal tube 13 all comprise surgical stainless steel, such as 304 grade surgical stainless steel or 316 grade surgical stainless steel. In accordance with one embodiment of the present invention, at least two needles (e.g., the distal needle 8 and the intermediate tube 10) are attached from larger to smaller diameter so as to create a transitional cone to facilitate the movement of viscous bulking material, such as material containing suspended beads or micro-spheres, through the transition-bore needle apparatus in a direction from the larger diameter tube to the smaller diameter needle. In the illustrated embodiment, three needles (i.e., the distal needle 8, the intermediate tube 10 and the proximal tube 13) are attached, preferably using an adhesive 34, from larger to smaller diameters so as to create a transitional cone to facilitate the movement of viscous materials through the transition-bore needle apparatus in a direction from the larger diameter needle to the smaller diameter needles. Other modified embodiments may incorporate a greater number of needles.

The lumen of the transition-bore needle apparatus 7 comprises both a portion of the lumen 19 of the distal needle 8 and a portion of the lumen 26 of the intermediate tube 10, as can be seen in FIG. 4. A juncture thus exists within the lumen of the transition-bore needle apparatus 7, where the diameter thereof transitions from a diameter of the intermediate tube 10 to a diameter of the distal needle 8. At this juncture, the proximal end 15 of the distal needle 8 terminates within the lumen 26 of the intermediate tube 10.

In the illustrated embodiment, the distal needle 8 comprises an inner diameter of about 0.008 inches and an outer diameter of about 0.016 inches. The distal needle 8 fits into the intermediate tube 10, which in the illustrated embodiment comprises an inner diameter of about 0.020 inches and an outer diameter of about 0.028 inches. In the presently preferred embodiment, the distal needle 8 protrudes distally about 3 mm from the intermediate tube 10. The intermediate tube 10 fits into the proximal tube 13, which as presently embodied comprises an inner diameter of about 0.50 inches, an outer diameter of about 0.032 inches, and a length of about 12 inches. The proximal tube 13 encloses the proximal end 22 of the intermediate tube 10. The proximal tube 13 preferably comprises three hypotubes, which may facilitate a tighter fit around the intermediate tube 10 and/or greater rigidity of the proximal tube 13.

A tissue stop 31 is preferably disposed about the distal needle 8 next to the distal end 23 of the intermediate tube 10. The tissue stop 31 preferably comprises a diameter, which is about the same as the diameter of the proximal tube 13. In alternative embodiments other diameters may be constructed. The tissue stop 31 preferably comprises a circular perimeter, but may have oval or rectangular perimeters in alternative embodiments. The tissue stop 31 preferably comprises a polymeric material, which is more flexible than, for example, stainless steel. In modified embodiments, the tissue stop 31 may comprise surgical stainless steel.

An angle between a plane of the tissue stop 31 and a longitudinal axis of the transition-cone needle assembly 7 is preferably less than ninety degrees and, preferably, less than about 45 degrees and, more preferably, about 60 degrees as shown in FIG. 4. The orientation of the tissue stop 31 is preferably selected so that a planar surface of the tissue stop will align longitudinally with the axis of the particular lumen that is being treated. In other words, a planar surface of the tissue stop 31 should rest flat on the surface of the tissue that is to be treated with the distal needle 8. The tissue stop 31 will help to prevent the needle from penetrating deeper into the tissue than is required or desired. A surgeon performing an injection procedure using, for example, a cystoscope and/or the methods/devices disclosed in U.S. application Ser. No. 09/825,484, entitled URETHRA SURGICAL DEVICE, which is commonly assigned and the contents of which are incorporated herein by reference, can view the tissue stop 31 for assistance in performing the injection at the proper angle and at the proper depth.

In a modified embodiment, the tissue stop 31 may be omitted so that only the difference in outer diameters between the distal needle 8 and the intermediate tube 10 effectively operate as a tissue stop. In yet another modified embodiment, the tissue stop can be secured about the intermediate tube 10, instead of being secured about the distal needle 8, so that a distal planar surface of the tissue stop is flush with the distal end 23 of the intermediate tube 10.

Figure 6B:
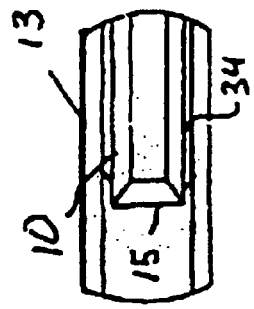
FIG. 6B is a cross-sectional view of a proximal end of a distal needle with edges chamfered at about a 45 degree angle from the longitudinal axis of the distal needle.
Figure 6A:
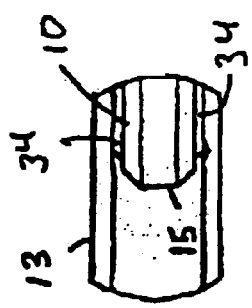
FIG. 6A is a cross-sectional view of a proximal end of a distal needle with edges beveled at about a 45 degree angle from the longitudinal axis of the distal needle.
Figure 6:
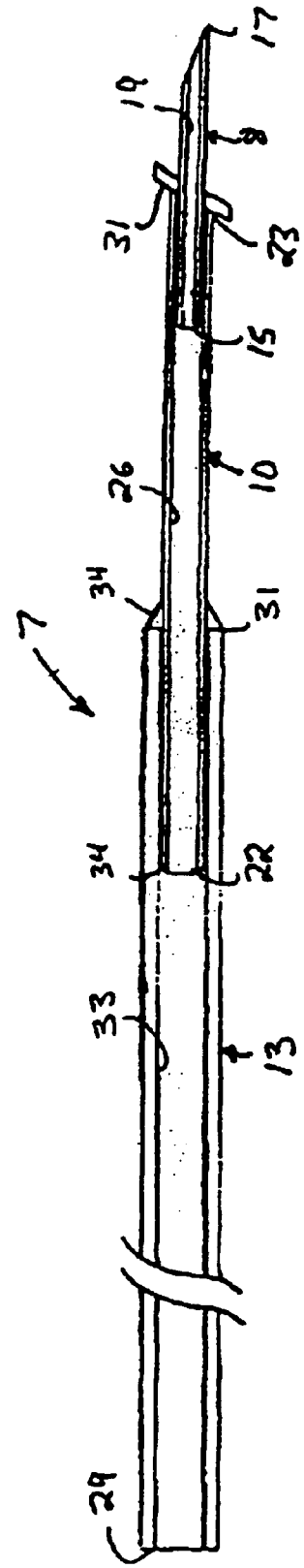
FIG. 6 illustrates a transition-bore needle apparatus for use in the treatment of urinary incontinence in accordance with the present invention.

As illustrated in FIG. 4, the proximal end 15 of the distal needle 8 is bevel-cut to improve the flow of viscous material through the lumen of the transition-bore needle apparatus 7, resulting in a bevel-cut needle transition 11. FIG. 4 illustrates a distal needle 8 with bevel-cut needle transition 11, cut at a 45 degree angle from the longitudinal axis of the distal needle 8. The bevel-cut may be performed, for example, by cutting the proximal end 15 of an initially cylindrical distal needle 8 at an angle to the longitudinal axis of the distal needle 8. The ensuing bevel-cut needle transition 11 is at an angle less than ninety degrees and, preferably, less than sixty degrees, and more preferably, about 45 degrees. The distal needle 8 with bevel-cut needle transition 11 is then secured within the lumen 26 of the intermediate tube 10, through the application of adhesive material between the outer surface of the distal needle 8 and inner surface of the intermediate tube 10 at their contacting surfaces. In modified embodiments, the angle may be reduced to, for example, 30 degrees or 15 degrees from the longitudinal axis of the distal needle 8. In even further embodiments, the proximal end may not be bevel cut so that the proximal end is oriented at approximately a 90 degree angle with respect to the longitudinal axis of the needle, as shown in FIGS. 6, 6A, and 6B, where like numbers designate like parts.

Figure 4A:
FIG. 4A is a cross-sectional view of a proximal end of a distal needle having a bevel-cut transition, which includes an edge that is beveled at about a 45 degree angle from a longitudinal axis of the needle.

According to another aspect of the present invention, the proximal end 15 of the distal needle 8 with bevel-cut needle transition 11 is beveled to improve a flow of viscous material through the lumen of the transition-bore needle apparatus 7. FIG. 4A and FIG. 6A are cross-sectional views of needle transitions 11 with the edges beveled at a 45 degree angle from the longitudinal axis of the distal needle 8. The beveling may be performed by filing the edge of the needle transition 11 to an angle less than ninety degrees and, preferably, less than sixty degrees, and more preferably, about 45 degrees. In modified embodiments, the angle may be reduced to, for example, 30 degrees or even about 15 degrees from the longitudinal axis of the distal needle 8. After the proximal end 15 of the distal needle 8 is beveled, the distal needle 8 may then be secured within the lumen 26 of the intermediate tube 10, through the application of adhesive material between the outer surface of the distal needle 8 and inner surface of the intermediate tube 10 at their contacting surfaces. In modified embodiments, the angle may be reduced to, for example, 30 degrees or even about 15 degrees from the longitudinal axis of the distal needle 8. Additionally, the needle may be fixed by swaging the proximal end of the needle in the distal end of the intermediate tube.

In accordance with another aspect of the present invention, the proximal end 15 of the distal needle 8 with bevel-cut needle transition 11 is chamfered to improve a flow of viscous material through the lumen of the transition-bore needle apparatus 7. FIG. 4B and FIG. 6B are cross-sectional views of a needle transition 11 with edges chamfered at a 45 degree angle from the longitudinal axis of the distal needle 8. The chamfering may be performed by filing the needle transition 11 to an angle less than ninety degrees and, preferably, less than sixty degrees, and more preferably, about 45 degrees. In modified embodiments, the angle may be reduced to, for example, 30 degrees, or even about 15 degrees from the longitudinal axis of the distal needle 8.

In yet another aspect of the present invention, the proximal end 15 of the distal needle 8 with needle transition 11 is both chamfered and beveled, in accordance with the structures discussed in the preceding paragraphs, to thereby improve a flow of viscous material through the lumen of the transition-bore needle apparatus 7.

In another embodiment, the proximal end 22 of the intermediate tube 10 is preferably bevel-cut, similarly to that described above in connection with the proximal end 15 of the distal needle 8, producing bevel-cut needle transition 25.

In alternative embodiments, the intermediate tube 10 with bevel-cut needle transition 25 is preferably beveled and/or chamfered, similarly to that described above in connection with the proximal end 15 of the distal needle 8 with bevel-cut needle transition 43. In modified embodiments, only the proximal end 15 of the distal needle 8 with bevel-cut needle transition 43 is beveled and/or chamfered, and the proximal end 22 of the intermediate tube 10 with bevel-cut needle transition 25 is neither beveled nor chamfered.

Figure 5:
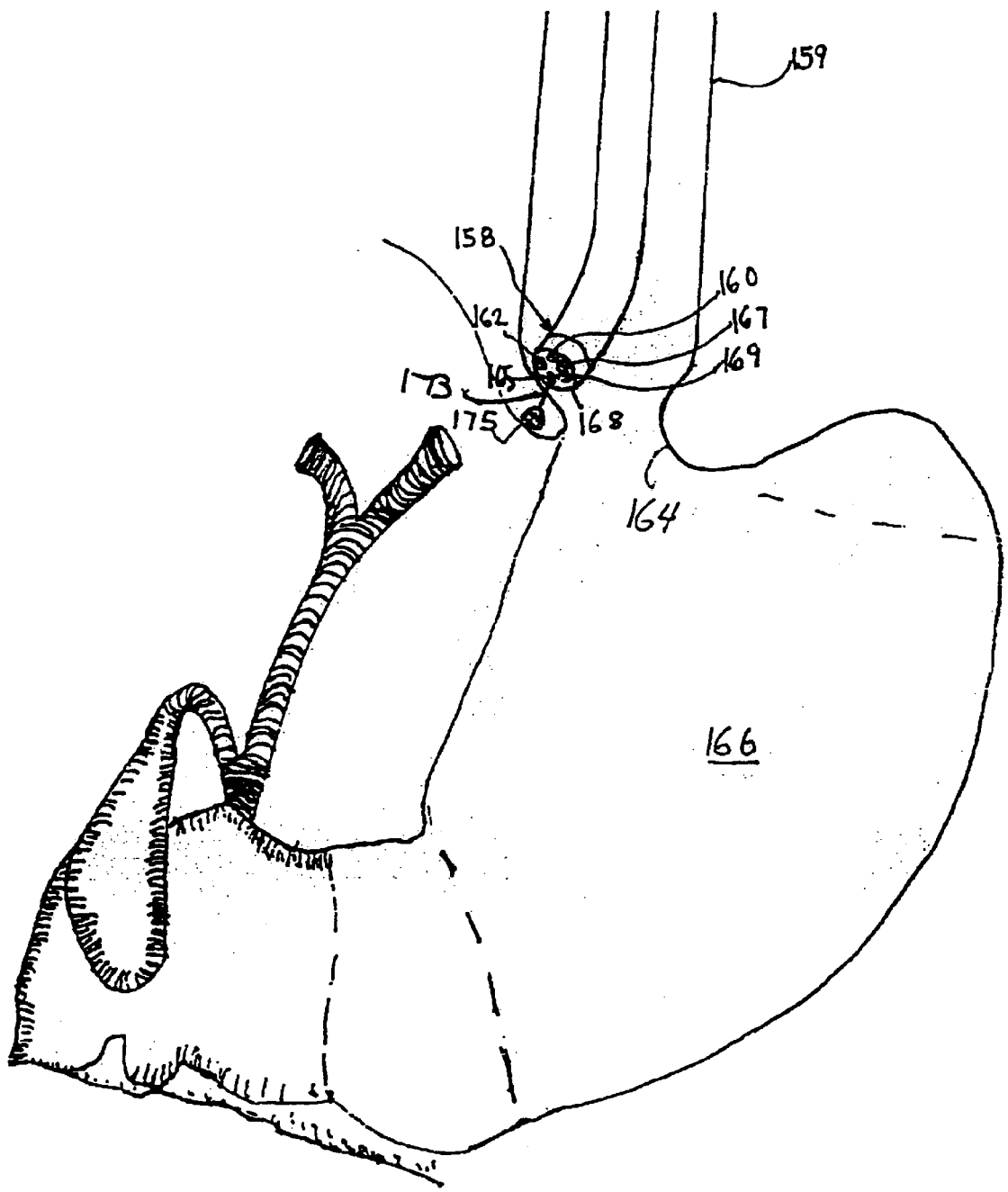
FIG. 5 illustrates an elongated flexible syringe disposed within a gastroscope for use in the urethra to treat urinary incontinence in accordance with the present invention.

FIG. 5 illustrates a gastroscope 158 inserted through an esophagus 159 of a patient. The gastroscope 158 is positioned near the patient's lower esophageal sphincter 164 just above the body of the stomach 166. The injection facilitation apparatus 17 of the present invention is used in conjunction with a syringe and the gastroscope 158 of FIG. 5.

The gastroscope 158 in the illustrated embodiment is constructed to be flexible and to be capable of bending, for example, one hundred eighty degrees. Although other scopes and surgical devices suitable for insertion and manipulation within body passages may be used in accordance with the present invention, the presently illustrated surgical device comprises a gastroscope 158 having a flexible, cylinder body with a distal end 168 for facilitating surgical procedures within a body passage. In the illustrated embodiment, the gastroscope 158 comprises an Olympus GIF-K Gastroscope.

The distal end 168 in the illustrated embodiment comprises five openings, but as few as two openings may be incorporated in modified embodiments. An objective lens 160 is enclosed in a first one of the openings to provide a visual pathway through the lumen and of the surgical site of interest. The gastroscope 158 further comprises another opening for providing a suction and/or working channel 165. Also provided at the distal end 168 is a channel for accommodating a light guide 162, which carries light to the distal end 168 for facilitating viewing of the treatment area through the visual passageway. The light guide 162 preferably comprises a fiber optic light guide. Alternatively a LED, or other bulb, or other light source may be incorporated. A water-feeding nozzle 169, which directs pressurized water across the objective lens 160 to clear debris and an air-feeding nozzle 167 are also housed within two respective channels of the gastroscope 158. The air-feeding nozzle 167 can be used to direct pressurized air across the objective lens 160 to remove moisture and to provide, in accordance with one application, distension of the cavity being examined.

An elongated flexible syringe in accordance with the present invention may be inserted through the working channel 165 for dispensing a somewhat viscous material into the surgical site, which in FIG. 5 comprises a vicinity of the lower esophageal sphincter 164. In the presently preferred embodiment, the elongated flexible syringe may have a length of, for example, about 1 meter to allow the elongated flexible syringe to extend through the esophagus and to the lower esophageal sphincter 164.

The user presses the hand-held compressing structure 90 to thereby move the movable rod 78 distally into the elongated flexible syringe chamber 100. Distal movement of the movable rod 78 forces viscous material within the elongated flexible syringe 70 to pass distally out of the elongated flexible syringe 70 and through the transition-bore needle apparatus. The elongated flexible syringe in the illustrated embodiment comprises a flexible material, such as a polymeric material, to facilitate maneuverability of the gastroscope 158. Injection procedures and apparatus, which utilize an elongated catheter and an accompanying syringe for treating, for example, urinary incontinence, and which are suitable for use with the elongated flexible syringe 70 for urethral applications, are described in co-pending U.S. application Ser. No. 09/825,484, entitled URETHRA SURGICAL DEVICE, filed Apr. 2, 2001, the contents of which are expressly incorporated herein by reference.

A needle 173, which may correspond for example to the needle 8 of FIG. 4, is disposed at a distal end of the elongated flexible syringe for transferring viscous or other material from the elongated flexible syringe into tissue. The needle 173 penetrates into the tissue near the lower esophageal sphincter to inject a bulge or bolus 175 of bulking agent, as shown in FIG. 5. Additional bulking agent injections are formed around the lower esophageal sphincter 164 to thereby bulk up the tissue in the vicinity of the lower esophageal sphincter.

The needle preferably penetrates through the mucosa but not through the muscle layers of the lower esophageal sphincter 164, to thereby enable the injection of bulking material between these tissues. In modified embodiments, the needle may further be placed into the layers of muscle of the lower esophageal sphincter to facilitate the injection of bulking agent into these tissues as well. In urethral procedures, the needle preferably penetrates through the mucosa but not through the muscle layers of the urinary sphincter, to thereby facilitate the injection of bulking material between these tissues; and in modified embodiments, the needle is further inserted into the layers of muscle of the urinary sphincter to facilitate the injection of bulking agent into these tissues as well. Uses of the elongated flexible syringe 70 are not limited to the above examples; the invention encompasses other foreseeable uses such as injections of viscous or other materials through elongated flexible syringes into the colon, vagina, vessels, and other lumen structures.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claimed is:

1. A transition-bore needle system for passing a viscous material into a patient, comprising a proximal end, a distal end, and a lumen extending from the proximal end to the distal end, wherein a diameter of the proximal end of the transition-bore needle apparatus is greater than a diameter of the distal end of the transition-bore needle apparatus, wherein the proximal portion of the transition-bore needle apparatus comprises a first needle having a first diameter, and distal portion of the transition-bore needle apparatus comprises a second needle having a second diameter, and wherein the proximal end of the first needle is bevel cut at a non-perpendicular angle to the longitudinal axis of the first needle.

2. The system of claim 1, wherein the proximal end of the second needle is bevel cut at a non-perpendicular angle to the longitudinal axis of the second needle.

3. The system of claim 2, wherein the bevel cut of the proximal end of the second needle creates a gradual transition from the diameter of the first needle to the diameter of the second needle.

4. The system of claim 2, further comprising a beveled edge at the bevel cut of the second needle.

5. The system of claim 2, further comprising a chamfered edge at the bevel cut of the second needle.

6. The system of claim 2, further comprising a beveled edge and a chamfered edge at the bevel cut of the second needle.

7. The system of claim 1, further comprising a tissue stop disposed about the transition-bore needle apparatus to control a distance to which the transition-bore needle apparatus may be inserted into a target site of a patient.

8. The system of claim 1, further comprising an elongate flexible chamber attached to the proximal end of the transition-bore needle apparatus and dimensioned to be inserted into a duct of a patient.

* * * * *